United States Patent
Vantard et al.

(10) Patent No.: US 9,162,020 B2
(45) Date of Patent: Oct. 20, 2015

(54) METHOD AND APPARATUS FOR CONTROLLING AN EXTRA-CORPOREAL BLOOD TREATMENT IN A MEDICAL DEVICE

(75) Inventors: Georges Vantard, Villefontaine (FR); Bernard Bene, Irigny (FR)

(73) Assignee: Gambro Lundia AB, Lund (SE)

( * ) Notice: Subject to any disclaimer, the term of this patent is extended or adjusted under 35 U.S.C. 154(b) by 69 days.

(21) Appl. No.: 13/175,131

(22) Filed: Jul. 1, 2011

(65) Prior Publication Data

US 2012/0010554 A1    Jan. 12, 2012

(30) Foreign Application Priority Data

Jul. 8, 2010 (EP) .................................. 10007040

(51) Int. Cl.
*A61M 1/16* (2006.01)
*A61M 1/36* (2006.01)

(52) U.S. Cl.
CPC ............... *A61M 1/16* (2013.01); *A61M 1/1607* (2014.02); *A61M 1/1609* (2014.02); *A61M 1/3609* (2014.02); *A61M 2205/33* (2013.01); *A61M 2205/52* (2013.01); *A61M 2205/60* (2013.01)

(58) Field of Classification Search
CPC ... A61M 1/16; A61M 1/3609; A61M 1/1607; A61M 1/1609; A61M 2205/33; A61M 2205/60
USPC ...................... 604/4.01, 5.04, 6.09, 6.1, 6.11; 210/645, 646; 422/44
See application file for complete search history.

(56) References Cited

U.S. PATENT DOCUMENTS

| 4,821,795 | A | | 4/1989 | Lu |
| 5,366,630 | A | * | 11/1994 | Chevallet ...................... 210/645 |
| 6,671,549 | B2 | * | 12/2003 | Van Dam et al. ............... 607/25 |
| 7,435,235 | B2 | * | 10/2008 | Sternby ........................ 604/6.09 |

(Continued)

FOREIGN PATENT DOCUMENTS

| DE | 19814687 C1 | 2/1999 |
| DE | 102005001051 A1 | 7/2006 |

(Continued)

OTHER PUBLICATIONS

Cheung, A.K., "Stages of Future Developments in Haemodialysis," *Nephrology Dialysis Transplantation*, Supp. 8, 1996, pp. 52-58.

*Primary Examiner* — Leslie Deak
(74) *Attorney, Agent, or Firm* — Mueting, Raasch & Gebhardt, P.A.

(57) ABSTRACT

Apparatus for controlling an extra-corporeal blood treatment in a medical device, comprising a blood treatment device (7), an extra-corporeal blood transport line (4), a fluid transport line (3) for a treatment fluid for the blood, at least a sensor adapted to provide a measure (M) correlated to at least a treatment parameter of the extra-corporeal blood treatment and/or of the treatment device (7) in the medical device (1), at least one storage memory (29), and at least a control device (28), operatively connected at least with the storage memory (29) and with the sensor, and configured for receiving the measure (M) from the sensor, correlating the measure (M) with referential data (R) of the treatment device for the treatment parameter provided by the at least one storage memory (29), and correlating the measure (M) with patient historical data (H) for the treatment parameter for obtaining an information representative of the quality of the extra-corporeal blood treatment.

32 Claims, 1 Drawing Sheet

(56) References Cited

U.S. PATENT DOCUMENTS

| | | | |
|---|---|---|---|
| 7,540,851 B2 * | 6/2009 | O'Mahony et al. | ..... 604/6.09 |
| 2003/0023461 A1 | 1/2003 | Quintanilla | |
| 2003/0028082 A1 | 2/2003 | Thompson | |
| 2003/0216623 A1 | 11/2003 | Abraham-Fuchs | |
| 2004/0039602 A1 | 2/2004 | Greenberg | |
| 2004/0057037 A1 | 3/2004 | Ohishi | |
| 2004/0059599 A1 | 3/2004 | McIvor | |
| 2005/0113734 A1 | 5/2005 | Brugger | |
| 2006/0059145 A1 | 3/2006 | Henschke | |
| 2006/0224326 A1 | 10/2006 | St. Ores | |
| 2007/0135750 A1 | 6/2007 | Kraemer | |
| 2008/0071209 A1 | 3/2008 | Moubayed | |
| 2008/0149551 A1 | 6/2008 | Brugger | |
| 2009/0076856 A1 | 3/2009 | Darby | |
| 2010/0282834 A1 | 11/2010 | Devergne | |
| 2011/0105979 A1 * | 5/2011 | Schlaeper et al. | ..... 604/5.01 |

FOREIGN PATENT DOCUMENTS

| | | |
|---|---|---|
| EP | 1 396 274 A1 | 3/2004 |
| EP | 1396274 | 3/2004 |
| EP | 1 396 274 B1 | 6/2005 |
| EP | 1 500 029 B1 | 4/2007 |
| EP | 1 500 025 B1 | 7/2008 |
| FR | 2 915 105 A1 | 10/2008 |
| GB | 2 301 685 A | 12/1996 |
| JP | 1134198 | 5/1989 |
| JP | 2002-163370 | 6/2002 |
| JP | 2005-276180 | 10/2005 |
| WO | WO 95/24010 | 9/1995 |
| WO | WO 00/03344 | 1/2000 |
| WO | WO 01/49368 A1 | 7/2001 |
| WO | WO 01/69513 A2 | 9/2001 |
| WO | WO 01/69513 A3 | 10/2002 |
| WO | WO 2004/070549 A2 | 8/2004 |
| WO | WO 2004/089445 A1 | 10/2004 |
| WO | WO 2004/070549 A3 | 6/2005 |
| WO | WO 2005/118054 A1 | 12/2005 |
| WO | WO 2008/009380 A1 | 1/2008 |
| WO | WO 2008/036658 A2 | 3/2008 |
| WO | WO 2008/036658 A3 | 6/2008 |
| WO | WO 2008/087470 A1 | 7/2008 |
| WO | WO 2008/129344 A1 | 10/2008 |
| WO | WO 2009/081241 A1 | 7/2009 |
| WO | WO 2010/028860 A1 | 3/2010 |
| WO | WO 2010/053626 A2 | 5/2010 |

* cited by examiner

METHOD AND APPARATUS FOR CONTROLLING AN EXTRA-CORPOREAL BLOOD TREATMENT IN A MEDICAL DEVICE

TECHNICAL FIELD

Methods and apparatus for controlling an extra-corporeal blood treatment in a medical device are described herein. The medical device may be, for example, a machine for extra-corporeal blood treatment, for treatment of renal or liver insufficiency or for receiving and storing liquid from a donor.

BACKGROUND

As it is known in the art, patients suffering from kidney failure or renal insufficiency, or patients suffering of particular pathologies should be submitted to specific treatments. More in detail, it is known to treat blood of a patient in an extra-corporeal circuit in order to carry out ultrafiltration, haemodialysis, haemofiltration, haemodiafiltration, plasmapheresis, blood component separation, blood oxygenation, or other treatments. Extra-corporeal blood treatment means taking the blood from a patient, treating the blood outside the patient, and eventually returning the treated blood to the patient. Normally, blood is removed from a blood vessel, through a withdrawal or arterial line of an extra-corporeal circuit, passed through a blood-treating unit and returned to another or to the same blood vessel by a venous line. Extra-corporeal blood treatment is typically used to extract undesirable matter or molecules from the patient's blood, and/or to add beneficial matter or molecules to the blood. Extra-corporeal blood treatment is used with patients incapable of effectively eliminating matter from their blood, for example in the case of a patient who is suffering from temporary or permanent kidney failure. These and other patients may undergo extra-corporeal blood treatment to add to or to eliminate matter from their blood, to maintain an acid-base balance or to eliminate excess body fluids, for instance.

Extra-corporeal blood treatment is typically, but not necessary, performed by sampling the patient's blood in a continuous flow, by introducing the blood into a primary chamber of a treatment device or filter in which the blood comes into contact with a semi-permeable membrane. The semi-permeable membrane selectively lets the unwanted matter contained in the blood pass through the membrane, from the primary chamber to the secondary chamber, and also selectively lets the beneficial matter contained in the liquid going into the secondary chamber pass through the membrane to the blood going into the primary chamber, according to the type of treatment. Generally the same machine may perform a number of different extra-corporeal blood treatments. In ultrafiltration (UF) treatment, the unwanted matter and excess water are eliminated from the blood by convection through the membrane in the secondary chamber. In haemofiltration (HF) treatment, the blood comes into contact with the semi-permeable membrane as in UF, and the beneficial matter is added to the blood, typically by the introduction of a substitution fluid into the blood, either before, or after its passage through the filter and before it is returned to the patient. In haemodialysis (HD) treatment, a secondary fluid containing the beneficial matter is introduced into the filter's secondary chamber. The blood's unwanted matter and the excess water cross the semi-permeable membrane and are removed by/with the exhaust secondary fluid, and the beneficial matter of the fresh secondary fluid may cross the membrane the other way round and penetrate into the blood.

In haemodiafiltration (HDF) treatment, the blood and the secondary fluid exchange elements as in HD, and further, matter is added to the blood, typically by introducing a fluid into the treated blood before it is returned to the patient as in HF, and the unwanted matter is also eliminated from the blood by convection. In each treatment, the secondary fluid goes through the filter's secondary chamber and receives the blood's unwanted matter and excess water crossing the membrane. This liquid is then extracted from the filter: it is commonly called waste, and is sent to a drain or to a bag then intended to be discharged into a drain. In fluid transport lines of medical devices, pumps are usually used in order to pump different fluids, such as blood, treatment liquids, waste liquids, along the transport lines. Such pumps may be for example positive displacement pumps (peristaltic pumps), volumetric pumps, piston type pumps, syringes, etc.

One aspect of known extra-corporeal blood treatments is determination and control of various treatment parameters during blood treatment, since it may be useful for the quality of the medical treatment if each treatment parameter remains between maximum and/or minimum threshold values in a correct relation with each other. In fact, deviations in treatment parameters may impair the quality of the medical treatment. Examples of treatment parameters that may be monitored include, but are not limited to: fluid flow rates in different lines of the circuit, ionic dialysance of the dialyzer, clearance of the dialyzer, water permeability (UF coefficient) of the dialyser membrane, blood pressure drop of the dialyzer, etc. It is known to provide medical devices with sensors and control means that allow respectively to measure and to monitor various treatment parameters, and it is known to configure the control means to carry out a specific action, like providing an alarm (for example a sound and/or a message) if a predetermined treatment parameter deviates from a normal value (e.g., above a certain limit). It is to be noted that the values assumed by various parameters during an extra-corporeal blood treatment depend upon many different aspects, including the type of dialyzer, the type of pump and the pump rate, the type and number of further components mounted in the circuit, the specific patient undergoing the treatment, and also further aspects.

Known methods and apparatuses for controlling treatment parameters are often not sufficiently precise, since the variability of the parameters due to the above different factors influence the reliability of the control and may lead to false alarms and/or to lack of alarm in potentially harmful situations.

SUMMARY

Extra-corporeal blood treatment circuits are described herein, but the scope of the invention should not be limited to this application.

Methods and apparatus for controlling an extra-corporeal blood treatment in medical devices that preferably address at least one of the above stated problems are described herein. In some embodiments, the methods and apparatus described herein for controlling an extra-corporeal blood treatment in a medical device may provide precise and safe control of treatment parameters. In some embodiments, the methods and apparatus described herein for controlling an extra-corporeal blood treatment in a medical device are very reliable. In some embodiments, the methods and apparatus described herein for controlling an extra-corporeal blood treatment in a medical device may avoid potentially harmful situations for the patient. In some embodiments, the methods and apparatus described herein for controlling an extra-corporeal blood treatment in a medical device are able to determine with high precision the situation of the extra-corporeal blood treatment, and, in case of undesired deviations in certain treatment parameters, to generate an alarm signal and/or to regulate automatically the treatment parameters to correct such deviations. In some embodiments, the methods and apparatus described herein for controlling an extra-corporeal blood treatment in a medical device provide a medical treatment of very high quality and safety for the patient. In some embodiments, the methods and apparatus described herein for controlling an extra-corporeal blood treatment in a medical device may be simply and cheaply realized. Other advantages and characteristics of the methods and apparatus described herein will become clear from reading the following description.

Methods and apparatus for controlling an extra-corporeal blood treatment in a medical device are described herein. In some embodiments, the apparatus may include a control device that comprises at least one storage memory and/or both storage memories. In some embodiments, the apparatus may be configured for univocally identifying a specific patient under treatment and for retrieving from a storage memory patient historical data relating to the specific patient under treatment.

In some embodiments, the apparatus may include a control device that is configured for correlating the measure also with referential data of said medical device for said treatment parameter provided by the at least one storage memory.

In some embodiments, the apparatus includes a control device that is configured for correlating the measure with the referential data of said medical device for obtaining a third deviation value and for comparing said third deviation value with a third threshold, in order to define the information representative of the quality of the extra-corporeal blood treatment.

In some embodiments of the apparatus, the referential data of said treatment device for said treatment parameter are defined with respect to the treatment device in combination with the specific medical device to which it is applied.

In some embodiments of the methods and apparatus described herein, at least said first threshold and/or second threshold are variable according to an auxiliary measure of an auxiliary treatment parameter received by the control device.

In some embodiments, a control device for an apparatus for controlling an extra-corporeal blood treatment in a medical device is configured for receiving a measure from a sensor, adapted to provide a measure correlated to at least a treatment parameter of the extra-corporeal blood treatment and/or of the treatment device in the medical device, correlating the measure with referential data of the treatment device for the treatment parameter provided by at least one storage memory, and correlating the measure with patient historical data for the treatment parameter during an extra-corporeal blood treatment of the patient, provided by the at least one storage memory, for obtaining at least an information representative of the quality of the extra-corporeal blood treatment.

In some embodiments, computer software as described herein may be configured for actuating the methods described herein.

In some embodiments of the methods described herein, the method may include univocally identifying a specific patient under treatment and to retrieve, from a storage memory, patient historical data relating to the specific patient.

In some embodiments of the methods described herein, the method may include obtaining referential data of said medical device for said treatment parameter and of correlating said measure also with said referential data of said medical device for said treatment parameter, for obtaining the information representative of the quality of the extra-corporeal blood treatment of the patient.

In some embodiments of the methods described herein, the method may include comparing the measure with the referential data of said medical device for said treatment parameter for obtaining a third deviation value and comparing the third deviation value with a third threshold for obtaining the information representative of the quality of the extra-corporeal blood treatment of the patient.

BRIEF DESCRIPTION OF THE DRAWINGS

Additional characteristics and advantages of the present invention will appear from the description of non-exclusive illustrative embodiments of the apparatus and methods described herein. This description will be given below with reference to the annexed drawings, which are supplied for information purposes and are thus not limiting.

DESCRIPTION OF ILLUSTRATIVE EMBODIMENTS

Figure 1:
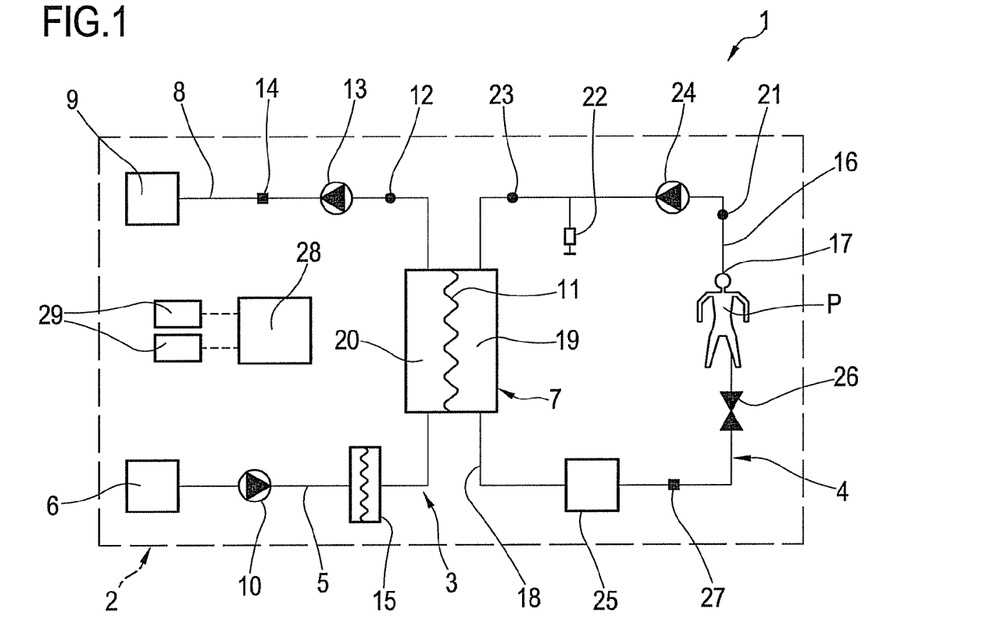
FIG. 1 represents an extra-corporeal blood treatment device according to one illustrative embodiment.

One illustrative embodiment of an apparatus for controlling an extra-corporeal blood treatment in a medical device 1 is depicted in FIG. 1. The medical device 1 may be, for example, a machine for blood treatment, such as a machine for treatment of kidney failure (for example a hemo(dia) filtration machine or a hemodialysis machine, for chronic or intensive therapy) or liver insufficiency or a plasmapheresis machine or in any case any other type of medical machine suitable for treatment of blood or a fluid, in particular a biological fluid. In the following description, reference will be made to a machine for extracorporeal treatment of blood in its essential components of known type and only partially mentioned. The medical device or equipment 1 comprises an extra-corporeal blood circuit 2 to be connected in use to the cardio-vascular system of a patient P to be treated (shown schematically in the drawings).

In practice, the patient P may be connected to the extra-corporeal blood circuit 2 via one or two needles, a catheter, a cannula, an implanted artificial access device or other equivalent access means, which allows withdrawal and return of blood from and to the patient P. In the embodiment of FIG. 1, the extra-corporeal blood circuit 2 comprises a hydraulic circuit for a treatment fluid or fluid transport line 3 and a blood circuit or extra-corporeal blood transport line 4. Note that the specific structure of the hydraulic circuit 3 is not to be construed as limiting and, therefore, circuits which are different from the one specifically shown in FIG. 1 might be used according to the functional and design requirements of each single medical apparatus.

The hydraulic circuit 3 optionally exhibits at least a supply channel 5, destined for transport of a treatment liquid from at least a source 6 towards a treatment station where one or more blood treatment units or treatment devices 7, such as filters or dialysers, operate. The circuit 3 further comprises at least a discharge channel 8 destined to transport a used liquid from the treatment device 7 towards an exit, schematically denoted by 9 in FIG. 1.

It should be noted that the supply channel 5 may be destined to cooperate with means for moving a fluid, such as at least a pump 10, for example a positive displacement pump, such as in particular a peristaltic pump, or a gear or diaphragm pump. A branch may be present downstream of the pump 10 and along the circulation direction, which divides the primary sterile fluid circuit into an inlet branch and an infusion branch (not illustrated but of known type). The infusion branch is connected to the blood removal line (arterial line) and/or the blood return line (venous line) of the blood circuit and enables an infusion to be obtained directly into the blood (before and/or after the blood treatment device or dialyser 7) using sterile fluid. The input branch brings the sterile fluid directly to the blood treatment stations for exchange through the membrane 11. A selector (for example a valve element and/or clamps and/or means for moving, such as one or more pumps) may preferably be present for determining the percentage quantities of fluid flow in the infusion branch and the input branch.

The fluid for dialysis thus enters the discharge channel 8 of the circuit and crosses a pressure sensor 12 provided for control of the functioning of the line. There are, therefore, further fluid movement means present, for example a drainage pump 13 which may control the flow in the discharge channel 8 of the circuit. The drainage pump 13 may, in general, be a positive displacement pump, such as, for example, a peristaltic pump, a gear pump, a diaphragm pump, etc. The fluid to be eliminated thus crosses a blood leak detector 14 and is conveyed towards the exit 9. The treatment fluid (dialysis fluid or replacement fluid) may be purified before use by one or more ultrafilters 15.

Other known elements, such as conductivity meters, flow meters, bypass lines and valves may be included in the hydraulic circuit.

The hydraulic circuit 3 cooperates with a blood circuit 4 which is also schematically represented in FIG. 1 in its basic components. The specific structure of the blood circuit is also not required, and thus, with reference to FIG. 1, a brief description of a possible embodiment of the circuit is provided, which should however be considered to be provided purely by way of non-limiting example.

The blood circuit 4 of FIG. 1 comprises an arterial line 16 for removing blood from a vascular access 17 of a patient and a venous line 18 predisposed to return the treated blood to the vascular access. The blood circuit of FIG. 1 further comprises a first chamber or blood chamber 19, of the blood treatment device 7 whose second chamber 20 is connected to the hydraulic circuit 3. In greater detail, the arterial line 16 is connected to the inlet of the blood chamber 19, while the venous line 18 is connected in outlet to the blood chamber 19. In turn, the supply channel 5 is connected in inlet to the second chamber 20, while the discharge channel 8 is connected in outlet to the second chamber. The blood treatment device 7, for example a dialyser or an ultrafilter or a plasma filter or a hemofilter or a hemodiafilter, comprises, as mentioned, the two chambers 19 and 20, which are separated by a semi-permeable membrane 11, for example a hollow-fibre or plate-type membrane. A blood pressure sensor 21 is located on the arterial line 16 along the circulation direction of the blood from the removal zone (vascular access) towards the blood treatment device 7.

The arterial line 16 may be further connected to a device for administering an anticoagulant 22, for example a syringe pump for providing appropriate anticoagulant doses (heparin). The arterial line may thus be provided, optionally, with a further pressure sensor 23 (arranged between a pump 24 and the device 7) for surveying the correct flow internally of the blood circuit.

The blood circuit may also comprise one or more air separators 25: the example of FIG. 1 shows a separator 25 on the venous line 18, upstream of a safety valve 26. The treated blood, exiting from the air separator device 25, crosses an air bubble sensor 27, provided to check for the absence of dangerous formations internally of the treated blood, which must be returned into the patient's blood circuit. In particular, should the air bubble sensor 27 reveal the presence of faults in the blood flow, the machine, via the safety valve 26 (which might be a cock, a clamp or the like) would be able immediately to block blood passage in order to prevent any type of consequence to the patient. The valve 26 may always be closed in the venous line should, for example for safety reasons, it becomes necessary to interrupt blood return to the vascular access 17.

The means 3 for fluid treatment may also comprise one or more blood pump 24, for example, positive displacement pumps such as peristaltic pumps. In the example of FIG. 1, there is a pump 24 on the arterial line 16. In general, the hydraulic circuit 3 is housed internally in the machine body, while the blood circuit 4 is borne on a front panel of the machine body which also supports the peristaltic pump or pumps 24. The treatment device 7 may be removable and physically supported, by rapid-attachment means (of known type) arranged, for example, on a lateral wall of the machine structure itself. The treatment device 7, in operating conditions of blood treatment, is connected both to the hydraulic circuit and to the blood circuit as already briefly mentioned.

As is known, the means for fluid treatment comprise the cited sensors (such as the pressure sensors, blood leak detector, pump speed sensors, flow meters, conductivity meters, transmembrane pressure sensors, blood volume sensors, etc) for detecting functioning parameters of the medical machine 2 and also the cited actuators (pumps, clamps, valves, syringe, etc) for intervening in order to modify the functioning parameters of the machine 2.

The medical machine 2 comprises a control unit or control device 28, which is programmed at least to send command signals and to receive data from the means for fluid treatment. The control unit 28 is thus active at least on the blood circuit and in particular is responsive to the pressure sensor 21, active for giving input to the blood pump 24, to the heparin infusion device 22, responsive to the further pressure sensor 23 as well as responsive to the device for detecting the presence of air bubbles 27 and active for giving input to the closing element 26. The control unit 28 is also active on the pump 10, on any selector means present, responsive to the pressure sensor 12, active on the drainage pump 13 and will also receive information from the blood leak detector 14. Further, the control unit 28 is set up to control the hydraulic circuit 3 of the sterile fluid and in particular will receive in input the data read off by any balances present on the machine relating to the weight of the various containers which may be in use on the machine.

Apart from the control of the sensors and the actuators, the control unit 28 may preferably be predisposed to receive and control further sensors and actuators present on the machine in order to guarantee and monitor the functioning thereon and in particular to monitor different parameters of the extra-corporeal blood treatment. The machine for extra-corporeal treatment may be provided with a fluid balance system, of the type used in a machine for hemodialysis and hemo(dia)filtration, for control of the patient's weight loss during the treatment, for example a flow-meter type, or a variable-volume volumetric chambers system, or a system including balances, or other systems of known type.

The machine may be provided with a system, of known type, for on-line preparation of the treatment fluid (for example dialysis fluid and/or replacement fluid) starting from water and concentrates, and/or a system (of known type) for degassing and/or heating the fluids running through the system itself, and/or a purification system having one or more treatment fluid ultrafiltration stages. The machine may be provided with a disinfection/cleaning system (of known type, for example of a chemical or thermal type, supplied by a distribution network or a batch source of disinfecting agents/cleaners) of the hydraulic circuit 3. Purely by way of example there might also be a liquid loss sensor destined to detect any eventual breakages or damage to the hydraulic circuit, which sensor will then send the data on directly to the control unit 28 for subsequent processing.

The control unit 28 may, for example, comprise one or more digital micro processing units or one or more units of an analog and/or digital type. In practice, in reference to the example of a microprocessor unit, once the unit has completed a special program (for example a program coming from and residing outside the system or directly installed on the microprocessor or in one of its memories), it is programmed by defining a plurality of functional modules or blocks which constitute means each predisposed to perform respective operations. The medical machine may be provided with at least a display for viewing at least a part of the data received from the control unit 28 relating to the means for fluid treatment. Further, the medical machine will be provided with at least one and in general a plurality of devices for entering the data to be supplied to the control unit 28 in order to enable a user to generate the above-mentioned command signals for the means 3 for fluid treatment. The devices for entering data may be of various natures and be constituted, even in combination, by a keyboard, a mouse, keys and buttons and activations, or even a touch screen.

In particular the display or screen of the medical machine 2 displays a graphic user interface (GUI) which provides an intuitively-comprehensible display of at least a part of the data received from the control unit 28 relating to the sensors and the actuators on the fluid treatment circuit. Merely by way of non-limiting example, in a case in which a graphic user interface is used with a configuration of the touch screen, the display itself will be divided into various to areas exhibiting a plurality of touch keys and a plurality of pictograms, each for example associated to a relative touch key. The expression "touch screen" relates to a screen for data output, also used for input by means of direct selection using the fingers of parts (touch keys) of the screen display to send the commands for performing the user's requested action to the control unit 28.

The medical device may comprise further elements, such as return pressure sensors, dialysate pressure sensors, flow meters, etc.

As described herein, the apparatus comprises at least a sensor adapted to provide a measure M correlated to at least a treatment parameter of the extra-corporeal blood treatment and/or of the treatment device 7 in the medical device 1, at least one storage memory 29, and at least a control device 28 operatively connected at least with the storage memory 29 and with the sensor. According to the invention the control device 28 is configured for receiving the measure M from the sensor, correlating the measure M with referential data R of the treatment device 7 for the treatment parameter provided by the at least one storage memory 29, and correlating the measure M with patient historical data H for the treatment parameter during an extra-corporeal blood treatment of the patient P, provided by the at least one storage memory 29, for obtaining at least an information representative of the quality of the extra-corporeal blood treatment.

Information relating to the quality of the extra-corporeal blood treatment might be of any kind giving an indication to the operator about the way the treatment session is proceeding. For example, the quality may be assessed through a correlation of measure M with the referential data R, or through a correlation of the measure M with patient historical data H, for determining deviation values to be compared with thresholds; the result of the comparison will give an indication of the treatment quality. Indeed, as an example, the control unit knows that in case the deviation value is above a certain threshold, the treatment is not going on properly and some problems are, or should be, expected; this is an indication of poor quality. Vice versa, in case the comparison is acceptable (e.g., the deviation value is below the threshold), the treatment is proceeding as expected.

Of course threshold and comparisons might be more than one each, giving therefore rise to the possibility of discerning different levels of quality of the treatment (e.g. comparison below threshold X and over threshold Y, meaning medium treatment quality). This concept may be better appreciated in connection with the illustrative embodiments described below.

The at least one storage memory 29 comprises the referential data R of the treatment parameter at least for a disposable part of the treatment device 7 and the patient historical data H of the treatment parameter for at least a specific patient P. The apparatus may comprise two of the cited storage memories 29 operatively connected with the control device 28, a first storage memory comprising the referential data R and the second storage memory comprising the patient historical data H.

In some embodiments, the storage memories could be coincident and containing several data (at least the referential data and the patient historical data) or could be distinct one from the other; in this case the two memories might be in the same physical database or in distinct databases as well. In case of a single memory, the same might be physically included in the medical apparatus of might also be a remote database as well.

As mentioned, the blood treatment device 7 may be a dialyzer and the extra-corporeal blood treatment may be ultrafiltration, haemodialysis, haemofiltration, haemodiafiltration, plasmapheresis, blood component separation or blood oxygenation. The treatment parameter may be an ionic dialysance of a dialyzer, or a clearance of a dialyzer, or a water permeability (UF coefficient) of a dialyser membrane, or a blood pressure drop of a dialyzer.

Figure 2:
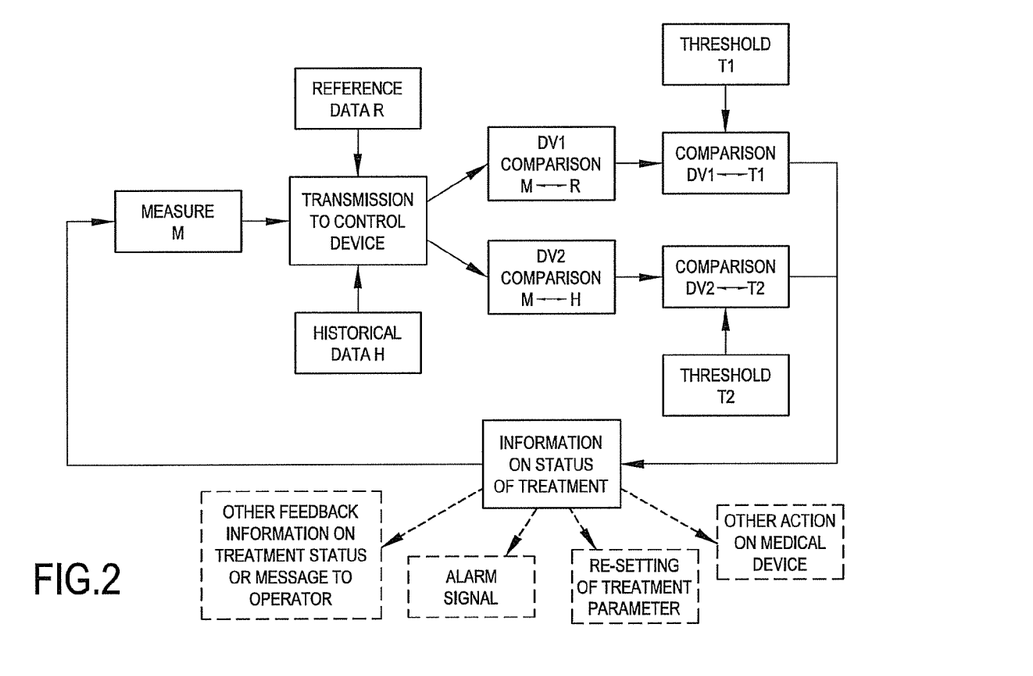
FIG. 2 is a flow chart representing a sequence of one illustrative embodiment of a method as described herein.

As illustrated in the flow chart of FIG. 2, the control device 28 is configured for correlating the measure M with the referential data R for obtaining a first deviation value DV1 and for comparing the first deviation value DV1 with a first threshold T1, and is further configured for correlating the measure M with patient historical data H for obtaining a second deviation value DV2 and for comparing the second deviation value DV2 with a second threshold T2.

The apparatus may further comprise an auxiliary sensor adapted to provide an auxiliary measure correlated to at least an auxiliary treatment parameter of the extra-corporeal blood treatment and/or of the treatment device 7 in the medical device 1. The control device 28 in this case may be configured for receiving the auxiliary measure from the auxiliary sensor and for selecting referential data R, of the treatment device for the treatment parameter, correlated with the auxiliary measure. In other words, since the value of the treatment parameter may depend upon the value of at least one auxiliary parameter, the referential data R may be provided as dependent upon the auxiliary measure of the auxiliary parameter (for example, the storage memory may have different values of the treatment parameter corresponding to different intervals of values of the auxiliary parameter). In a variant, the control device 28 may be configured for receiving the auxiliary measure from the auxiliary sensor and for evaluating the result of the correlations between the measure M and the referential data R of the treatment device and/or between the measure M and the patient historical data H in view of the auxiliary measure. Accordingly, the same result deriving from the above correlations may lead to different actions of the control device, depending at least upon the auxiliary measure of the auxiliary parameter. Also the threshold values may vary according to the auxiliary measure.

It is noted that the control device may receive and consider as explained above also a plurality of auxiliary measures of a plurality of auxiliary parameters influencing the treatment parameter, in order to further increase the reliability of the apparatus. It is also remarked that the effect of auxiliary parameters on the treatment parameter may be considered by the control device also in further ways, different from the examples above explained. The control device 28 may be configured for providing a message to an operator, a feedback signal, a control signal or an alarm signal when the information representative of the quality of the extra-corporeal blood treatment corresponds to a predetermined alarm value, and/or when the first DV1 and/or second deviation value DV2 have a predetermined correlation with the respective first T1 and second threshold T2. The control device 28 is configured for automatically varying predetermined treatment parameters and to re-adjust the blood treatment, when the information representative of the quality of the extra-corporeal blood treatment corresponds to a predetermined alarm value, and/or when the first and/or second deviation value DV1, DV2 have a predetermined correlation with the respective first and second threshold T1, T2. The control device 28 may be further configured for automatically recognizing the type of the treatment device 7 or the type of a disposable part of the treatment device 7 and for automatically selecting, from the first storage memory 29, referential data R of the treatment parameter for the type of the treatment device 7 or of the disposable part.

The apparatus may further be configured for identifying a specific patient under treatment and for retrieving, from the storage memory, patient historical data relating to the specific patient. Such identification may be carried out by known devices such as a card reader, by manual insertion in the control unit of the patient's name or identification number or code, etc.

According to a first variant of the embodiment, the apparatus for controlling an extra-corporeal blood treatment is configured to compare on line during a dialysis session a current ionic dialysance (depuration performance of the dialyser) with both the values stored in a historical data file of the patient under treatment and the values stored in the dialyser reference data base or referential. The name or reference of the patient under treatment may be set at the beginning of the treatment so that the control device may get from a storage memory the related historical data file of the patient. The patient historical data about ionic dialysance, may be available in a respective database, where a summary (a specific type of average value) may be calculated basing on a certain number of months of treatment. The control device may automatically recognize the type of dialyser or disposable filter mounted in the treatment device in order to access the correct data sheet of the dialyser or referential, i.e., the in vitro/in-vivo urea clearance at given blood & dialysate flow rates. Such HD clearances may be easily extrapolated taking in account the ultrafiltration flow rate by state of the art models. Beyond the "manufacturer data sheets", the "dialyser referential" could be further created more directly in term of "ionic dialysance" (by the compilation of huge number of in-vivo measurements on very stable patients without blood recirculation). In some embodiments, the control device 28 may be configured to deliver a message to the medical staff in case of deviations above a certain limit and/or to automatically re-adjust the relevant treatment parameters to reduce the deviation at an acceptable level. In other words at each measurement the ionic dialysance is compared to the dialyser referential data R and to the patient historical data H for calculation of a DV1 or DELTA(referential), i.e., a difference between the measured value and the referential value of the filter, and a DV2 or DELTA(historical), i.e., a difference between the measured value and the historical value of the patient, respectively. The positioning of these DELTA's in regards to given threshold values T1, T2 gives an indication of the quality of the treatment and may also trigger appropriate information/alarm messages and/or automatic parameters resetting. When DV1 Or DELTA(referential) is major that a predetermined T1 or THRESHOLD(referential) this could be due to: a miss-setting of prescribed blood flow rate (Qb), dialysate flow rate (Qd) and ultrafiltration flow rate (Qf), a reversed dialysate connection, blood coagulation problems, a significant blood recirculation, etc. In short, DELTA(referential) accounts mainly for deviations in the delivery of the prescribed treatment. When on the other side DV2 or DELTA (historical) is major than T2 or THRESHOLD(historical) this could be due to: a significant change of the prescribed dialysis parameters (blood flow Qb, dialysate flow Qd, ultrafiltration flow Qf, dialyzer surface area . . . ), a significant change in the vascular access status, a significant change of the EPO regimen, etc. In short, DELTA(historical) accounts mainly for deviations in the clinical status of the patient. In some embodiments, a combined use of two independent sources of information allows an accurate root-cause analysis in case of deviation of a given dialysis parameter (in this variant, the ionic dialysance). Further, in case DELTA(referential) is major than THRESHOLD(referential) and DELTA(historical) is inferior to THRESHOLD(historical), a display of a message such as "Dialyser performances below normal range"; "Check the conformity of the dialysers parameters with prescription", "Check proper positioning of blood needles and dialysate connectors", etc., may be envisaged. In case DELTA(referential) is inferior to THRESHOLD (referential) and DELTA(historical) is major than THRESHOLD (historical), display of a message such as "Unusual dialysis performances", "Check any change in prescribed dialysis parameters: Qb, Qf, Dialyzer size, Single Needle Dialysis (SN) vs Double Needle Dialysis (DN) . . . ", "Check any change in Erythropoietin (EPO) strategy", etc. may be envisaged, and/or triggering of an action with warning such as "Confirm change of prescribed dialysis parameters; "Confirm change in EPO strategy", etc. The automatic disposable recognition by the control device or by the machine allows to download the priming sequences for an automatic process or to download of the instruction for use and for information. The automatic recognition of all types of dialyser allows an automatic history file building per patient that could recap all relevant information from all session, such as: average ionic dialysance, Qb, Qd, Qf, T (temperature); average priming volume, average patient weight, average "total heparin infusion" used, average "transmembrane pressure" etc. Such recap may be made available to the operator. Further the control device 28 may offer an automatic customization of the control device 28 display thanks to the dialyser (treatment device 7) recognition. Further such recaps could be then consolidated into the dialyser "Referential". Further the automatic recognition of an hollow fiber dialyser (treatment device 7) could trigger a calculation and/or display of an estimation of a minimum Quf (ultrafiltration flow rate) preventing backfiltration, from the "referential" database and the actual setting for Qb and Qd. Further the automatic dialyser recognition could trigger a specific management and/or warning of an heparin pump, like detection of a condition of "no heparin in priming fluid" or of "delayed start of the heparin pump". Additionally when a specific anti-thrombogenic venous blood line is available and recognized by the ID reader, the proper combination of a specific dialyser and the anti-thrombogenic venous blood line could be checked by the control device 28 for a user recommendation and/or a security warning. Further recognition of a specific type of dialyser (treatment device 7) could trigger a recommendation and/or warning about the optimal prescription of Qd according to the prescribed patient P. According to what is stated above regarding the influence of auxiliary parameters on a treatment parameter, it is noted, for example, that the ionic dialysance values depends at least upon the blood flow value. Accordingly the control device may be configured for retrieving different referential data R for the ionic dialysance of the dialyser depending upon the blood flow value measured during the treatment. Otherwise, the control device may be configured for evaluating the results of the correlations between the measure M, referential data R and/or historical data H, in a different way depending upon the blood flow value measured during the treatment. According to a second variant of the embodiment, the apparatus for controlling an extra-corporeal blood treatment is configured to compare on line during a dialysis session a current water permeability (UF coefficient) of the dialyser membrane 11 with both the values stored in a historical data file of the patient P under treatment and the values stored in the dialyser reference data base or referential. The second variant is similar to the first variant, but in this case the water permeability is controlled instead of the ionic dialysance. Different factors govern the in-vivo UF coefficient of the dialyser during the dialysis session, such as the blood characteristics of the patient (blood viscosity, hematocrit, plasmatic protein concentration), blood clotting, etc. In order to detect abnormalities that could impair the quality or adequacy of the treatment, the UF coefficient may be monitored by looking at the actual transmembrane pressure (TMP) in relation to the actual ultrafiltration rate. The detected UF value is compared by the control device 28 with a value stored in the historical data file of the patient and a value stored in the dialyser reference data base. Abnormal high values could indicate a membrane leak or a low plasmatic protein (de-nutrition), while a low value could indicate a high blood hematocrit or viscosity (EPO regimen), a high protein concentration, a membrane fooling due to too high Quf, etc. In a third variant, similar to the first two variants, the parameter monitored and controlled by the control device 28 may be for example the blood pressure drop of the dialyser. Abnormal high values could indicate a high blood hematocrit or viscosity (EPO regimen), hollow fibers blocked by air (bad priming), a blood clotting (anticoagulation regimen), while a low value could indicate low blood hematocrit or viscosity (EPO regimen, de-nutrition, strong hemolysis), etc.

In some embodiments of the methods described herein, the method for controlling an extra-corporeal blood treatment in a medical device may include the steps of pumping blood of a patient P through an extra-corporeal blood transport line and through a blood treatment device 7, connected to the extra-corporeal blood transport line and to a fluid transport line for a blood treatment fluid, and sensing a measure M correlated to at least a treatment parameter of the extra-corporeal blood treatment in the medical device 1. The method further comprises the steps of obtaining referential data of the treatment device 7 for the treatment parameter, obtaining historical data of the patient P for the treatment parameter, correlating the measure M with the referential data R of the treatment device 7 and correlating the measure M with the patient historical data H of the patient P, for obtaining at least an information representative of the quality of the extra-corporeal blood treatment of the patient. The step of sensing a measure M correlated to at least a treatment parameter may be provided to sense a measure correlated to a ionic dialysance of a dialyzer, or to a clearance of a dialyzer, or to a water permeability (UF coefficient) of a dialyser membrane, or to a blood pressure drop of a dialyzer. The method may further comprise the steps of comparing the measure M with the referential data R for obtaining a first deviation value DV1 and comparing the first deviation value DV1 with a first threshold T1, and the steps of comparing the measure M with patient historical data H for obtaining a second deviation value DV2 and comparing the second deviation value DV2 with a second threshold T2. The method may further comprise the step of providing an alarm signal, a control signal or a feedback signal (by, for example, modifying the colour or aspect of information represented on a display) when the information representative of the quality of the extra-corporeal blood treatment corresponds to a predetermined alarm value, and/or when the first or second deviation value DV1. DV2 have a predetermined correlation with the respective first and second threshold T1, T2. The method may further comprise the step of automatically varying predetermined treatment parameters, to re-adjust the blood treatment, when the information representative of the quality of the extra-corporeal blood treatment corresponds to a predetermined alarm value, and/or when the first or second deviation value DV1. DV2 have a predetermined correlation with the respective first and second threshold T1, T2. The method may further comprise the steps of automatically recognizing the type of the treatment device 7 or the type of a disposable part of the treatment device 7 and of automatically selecting referential data of the treatment parameter for the type of the treatment device 7 or of the disposable part.

In some embodiments, the methods and apparatus described herein may provide one or more of the following advantages:

- a method and apparatus for controlling an extra-corporeal blood treatment in a medical device that may provide very precise control of treatment parameters;
- an apparatus and method that may be able to determine with high precision the exact status of an extra-corporeal blood treatment;
- an apparatus and method that may automatically send a signal and/or regulate the parameters of a medical treatment;
- an apparatus and method that may reduce possible mistakes in an extra-corporeal blood treatment;
- an apparatus and method that may carry out medical treatments with high reliability and reduced risks for the patient;
- an apparatus and method that may be simply realized and are not expensive.

The invention claimed is:

1. Apparatus for controlling an extra-corporeal blood treatment in a medical device, comprising:
   a blood treatment device, the blood treatment device being a dialyzer;
   an extra-corporeal blood transport line, having at least an arterial line configured to bring blood from a first access of a patient under treatment to said blood treatment device, a venous line configured to bring blood from said blood treatment device to a second access of the patient, and at least a first pump for moving blood in said extra-corporeal blood transport line;
a fluid transport line for a treatment fluid for said blood, the fluid transport line adapted to bring the treatment fluid from a source to said blood treatment device and from said blood treatment device to an exit, and at least a second pump for moving the treatment fluid in the fluid transport line;
at least a sensor adapted to provide a measure correlated to at least a treatment parameter of the extra-corporeal blood treatment or of the treatment device in the medical device;
at least one storage memory; and
at least a control device operatively connected at least with said storage memory and with said sensor;
wherein said control device is configured for:
receiving said measure from said sensor,
correlating said measure at least with referential data of said treatment device for said treatment parameter provided from said at least one storage memory to obtain a first deviation value (DV1),
comparing said first deviation value (DV1) with a first threshold (T1) to determine when the first deviation value (DV1) is less than or greater than the first threshold (T1),
correlating said measure with patient historical data of said patient under treatment for said treatment parameter during an extra-corporeal blood treatment of said patient under treatment, provided from said at least one storage memory, to obtain a second deviation value (DV2),
comparing said second deviation value (DV2) with a second threshold (T2) to determine when the second deviation value (DV2) is less than or greater than the second threshold (T2),
detecting the occurrence of a first event when the first deviation value (DV1) is greater than the first threshold (T1) and the second deviation value (DV2) is less than the second threshold (T2),
detecting the occurrence of a second event when the first deviation value (DV1) is less than the first threshold (T1) and the second deviation value (DV2) is greater than the second threshold (T2),
determining that a first root-cause of the first deviation value (DV1) and the second deviation value (DV2) is related to delivery of the extra-corporeal blood treatment to the patient under treatment when the occurrence of the first event is detected,
determining that a second root-cause of the first deviation value (DV1) and the second deviation value (DV2) is related to a deviation in a clinical status of the patient under treatment when the occurrence of the second event is detected.

2. Apparatus according to claim 1, wherein said at least one storage memory comprises at least said referential data of said treatment parameter at least for a disposable part of said treatment device and said patient historical data of said treatment parameter for at least a specific patient.

3. Apparatus according to claim 1, wherein said extra-corporeal blood treatment comprises ultrafiltration, haemodialysis, haemofiltration, haemodiafiltration, plasmapheresis, blood component separation or blood oxygenation.

4. Apparatus according to claim 1, wherein said treatment parameter is selected from the group consisting of a ionic dialysance of the dialyzer, a clearance of the dialyzer, a water permeability (UF coefficient) of the dialyser membrane, and a blood pressure drop of the dialyzer.

5. Apparatus according to claim 1, further comprising an auxiliary sensor configured to provide an auxiliary measure correlated to at least an auxiliary treatment parameter of the extra-corporeal blood treatment or of the treatment device in the medical device, said control device being configured for receiving said auxiliary measure from said auxiliary sensor and for selecting referential data, of said treatment device for said treatment parameter, correlated with said auxiliary measure, or being configured for receiving said auxiliary measure from said auxiliary sensor and for evaluating the result of the correlation between said measure and said referential data of said treatment device or between said measure and said patient historical data in view of said auxiliary measure.

6. Apparatus according to claim 1, comprising two of said storage memories operatively connected with said control device, a first storage memory comprising said referential data and a second storage memory comprising said patient historical data.

7. Apparatus according to claim 1, in which said control device is further configured for automatically recognizing the type of said treatment device or the type of a disposable part of said treatment device and for automatically selecting, from said storage memory, referential data of said treatment parameter for said type of said treatment device or of said disposable part or referential data of said treatment parameter for said type of said treatment device or of said disposable part when mounted to said medical device.

8. Apparatus according to claim 1, wherein the control device is further configured to generate a message to an operator regarding delivery of the extra-corporeal blood treatment to the patient under treatment when the control device detects occurrence of the first event.

9. Apparatus according to claim 1, wherein the control device is further configured to generate a control signal regarding delivery of the extra-corporeal blood treatment to the patient under treatment when the control device detects occurrence of the first event.

10. Apparatus according to claim 1, wherein the control device is further configured to generate a feedback signal regarding delivery of the extra-corporeal blood treatment to the patient under treatment when the control device detects occurrence of the first event.

11. Apparatus according to claim 1, wherein the control device is further configured to generate an alarm signal regarding delivery of the extra-corporeal blood treatment to the patient under treatment when the control device detects occurrence of the first event.

12. Apparatus according to claim 1, wherein the control device is further configured to generate a message to an operator regarding the deviation in a clinical status of the patient under treatment when the control device detects occurrence of the second event.

13. Apparatus according to claim 1, wherein the control device is further configured to generate a control signal regarding the deviation in a clinical status of the patient under treatment when the control device detects occurrence of the second event.

14. Apparatus according to claim 1, wherein the control device is further configured to generate a feedback signal regarding the deviation in a clinical status of the patient under treatment when the control device detects occurrence of the second event.

15. Apparatus according to claim 1, wherein the control device is further configured to generate an alarm signal regarding the deviation in a clinical status of the patient under treatment when the control device detects occurrence of the second event.

16. Method of controlling an extra-corporeal blood treatment in a medical device, the method comprising:
pumping blood of a patient under treatment through an extra-corporeal blood transport line and through a blood treatment device, connected to said extra-corporeal blood transport line and to a fluid transport line for a blood treatment fluid, said blood treatment device being a dialyzer,
sensing a measure correlated to at least a treatment parameter of the extra-corporeal blood treatment in the medical device,
obtaining referential data of said treatment device, or of a disposable part of said treatment device, for said treatment parameter,
obtaining historical data of said patient under treatment for said treatment parameter,
correlating said measure at least with said referential data of said treatment device to obtain a first deviation value (DV1),
comparing said first deviation value (DV1) with a first threshold (T1) to determine when the first deviation value (DV1) is less than or greater than the first threshold (T1),
correlating said measure with said patient historical data of said patient to obtain a second deviation value (DV2),
comparing said second deviation value (DV2) with a second threshold (T2) to determine when the second deviation value (DV2) is less than or greater than the second threshold (T2),
determining that a first root-cause of the first deviation value (DV1) and the second deviation value (DV2) is related to delivery of the extra-corporeal blood treatment to the patient under treatment when the first deviation value (DV1) is greater than the first threshold (T1) and the second deviation value (DV2) is less than the second threshold (T2),
determining that a second root-cause of the first deviation value (DV1) and the second deviation value (DV2) is related to a deviation in a clinical status of the patient under treatment when the first deviation value (DV1) is less than the first threshold (T1) and the second deviation value (DV2) is greater than the second threshold (T2).

17. Method according to claim 16, in which said sensing a measure correlated to at least a treatment parameter comprises sensing a measure correlated to a ionic dialysance of the dialyzer, or to a clearance of the dialyzer, or to a water permeability (UF coefficient) of the dialyser membrane, or to a blood pressure drop of the dialyzer.

18. Method according to claim 16, in which said referential data of said treatment device for said treatment parameter are defined with respect to the treatment device in combination with the specific medical device to which said treatment device is applied or with respect to an auxiliary measure of an auxiliary parameter influencing said treatment parameter.

19. Method according to claim 16, further comprising automatically recognizing the type of said treatment device or the type of a disposable part of said treatment device and of automatically selecting referential data of said treatment parameter for said type of said treatment device or of said disposable part or referential data of said treatment parameter for said type of said treatment device or of said disposable part when mounted to said medical device.

20. Method according to claim 16, wherein the method further comprises generating a message to an operator regarding delivery of the extra-corporeal blood treatment to the patient under treatment when the first deviation value (DV1) is greater than the first threshold (T1) and the second deviation value (DV2) is less than the second threshold (T2).

21. Method according to claim 16, wherein the method further comprises generating a control signal regarding delivery of the extra-corporeal blood treatment to the patient under treatment when the first deviation value (DV1) is greater than the first threshold (T1) and the second deviation value (DV2) is less than the second threshold (T2).

22. Method according to claim 16, wherein the method further comprises generating a feedback signal regarding delivery of the extra-corporeal blood treatment to the patient under treatment when the first deviation value (DV1) is greater than the first threshold (T1) and the second deviation value (DV2) is less than the second threshold (T2).

23. Method according to claim 16, wherein the method further comprises generating an alarm signal regarding delivery of the extra-corporeal blood treatment to the patient under treatment when the first deviation value (DV1) is greater than the first threshold (T1) and the second deviation value (DV2) is less than the second threshold (T2).

24. Method according to claim 16, wherein the method further comprises generating a message to an operator regarding the deviation in a clinical status of the patient under treatment when the first deviation value (DV1) is less than the first threshold (T1) and the second deviation value (DV2) is greater than the second threshold (T2).

25. Method according to claim 16, wherein the method further comprises generating a control signal regarding the deviation in a clinical status of the patient under treatment when the first deviation value (DV1) is less than the first threshold (T1) and the second deviation value (DV2) is greater than the second threshold (T2).

26. Method according to claim 16, wherein the method further comprises generating a feedback signal regarding the deviation in a clinical status of the patient under treatment when the first deviation value (DV1) is less than the first threshold (T1) and the second deviation value (DV2) is greater than the second threshold (T2).

27. Method according to claim 16, wherein the method further comprises generating an alarm signal regarding the deviation in a clinical status of the patient under treatment when the first deviation value (DV1) is less than the first threshold (T1) and the second deviation value (DV2) is greater than the second threshold (T2).

28. Apparatus for controlling an extra-corporeal blood treatment in a medical device, comprising:
a blood treatment device;
an extra-corporeal blood transport line having at least an arterial line configured to bring blood from a first access of a patient under treatment to the blood treatment device, a venous line configured to bring blood from the blood treatment device to a second access of the patient, and at least a first pump for moving blood in the extra-corporeal blood transport line;
a fluid transport line for a treatment fluid for the blood, the fluid transport line configured to bring the treatment fluid from a source to the blood treatment device and from the blood treatment device to an exit, and at least a second pump for moving the treatment fluid in the fluid transport line;
at least a sensor configured to provide a measure correlated to at least a treatment parameter of the extra-corporeal blood treatment or of the blood treatment device;
an auxiliary sensor configured to provide an auxiliary measure correlated to the blood treatment device in the medical device;
at least one storage memory; and at least a control device operatively connected at least with the storage memory, the sensor; and the auxiliary sensor, wherein the control device is configured to:
  receive the measure from said sensor,
  correlate the measure at least with referential data of the blood treatment device of said patient under treatment for the treatment parameter provided from the at least one storage memory, and
  correlate the measure with patient historical data for the treatment parameter during the extra-corporeal blood treatment to obtain information representative of quality of the extra-corporeal blood treatment;
  receive the auxiliary measure from the auxiliary sensor;
  select the referential data of the blood treatment device for the treatment parameter depending on the auxiliary measure; and
  obtain information representative of quality of the extra-corporeal blood treatment based on said correlations.

29. Apparatus for controlling an extra-corporeal blood treatment in a medical device, comprising:
  a blood treatment device;
  an extra-corporeal blood transport line having at least an arterial line configured to bring blood from a first access of a patient under treatment to the blood treatment device, a venous line configured to bring blood from the blood treatment device to a second access of the patient, and at least a first pump for moving blood in the extra-corporeal blood transport line;
  a fluid transport line for a treatment fluid for the blood, the fluid transport line configured to bring the treatment fluid from a source to the blood treatment device and from the blood treatment device to an exit, and at least a second pump for moving the treatment fluid in the fluid transport line;
  a sensor configured to provide a measure correlated to at least a treatment parameter of the extra-corporeal blood treatment or of the blood treatment device;
  an auxiliary sensor configured to provide an auxiliary measure correlated to an auxiliary treatment parameter of the extra-corporeal blood treatment or of the blood treatment device in the medical device;
  storage memory; and
  at least a control device operatively connected at least with the storage memory the auxiliary sensor, and the sensor; wherein the control device is configured to:
    receive the measure from said sensor,
    receive the auxiliary measure from the auxiliary sensor,
    correlate the measure at least with referential data of the blood treatment device to obtain a first deviation value (DV1,
    compare the first deviation value (DV1) with a first threshold (T1),
    correlate the measure with patient historical data of the patient under treatment to obtain a second deviation value (DV2),
    compare the second deviation value (DV2) with a second threshold (T2),
    evaluate the result of said correlations based on the auxiliary measure.

30. The apparatus of claim 29, wherein the control device is configured to alter the first and second threshold values based on the auxiliary measure.

31. Method of controlling an extra-corporeal blood treatment in a medical device, the method comprising:
  pumping blood of a patient under treatment through an extra-corporeal blood transport line and through a blood treatment device connected to said extra-corporeal blood transport line and pumping a blood treatment fluid through a fluid transport line to the blood treatment device to perform an extracorporeal blood treatment on the blood;
  sensing a measure correlated to at least a treatment parameter of the extra-corporeal blood treatment;
  sensing an auxiliary measure correlated to an auxiliary treatment parameter of the extra-corporeal blood treatment or of the blood treatment device in the medical device;
  obtaining referential data of the blood treatment device or of a disposable part of the blood treatment device for the treatment parameter;
  obtaining historical data of the patient under treatment for the treatment parameter;
  correlating the measure at least with the referential data to obtain a first deviation value (DV1);
  comparing the first deviation value (DV1) with a first threshold (T1);
  correlating the measure with the historical data of the patient under treatment to obtain a second deviation value (DV2);
  comparing said second deviation value (DV2) with a second threshold (T2);
  evaluating the result of said correlations based on the auxiliary measure.

32. The method of claim 31 comprising altering the first and second threshold values based on the auxiliary measure.

* * * * *